US00PP37640P2

(12) United States Plant Patent
Byrne et al.

(10) Patent No.: US PP37,640 P2
(45) Date of Patent: Aug. 25, 2026

(54) NECTARINE TREE NAMED 'TRH4D144WN'

(50) Latin Name: *Prunus persica*
Varietal Denomination: TRH4D144WN

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,292

(22) Filed: Sep. 22, 2025

(51) Int. Cl.
*A01H 5/08* (2018.01)

(52) U.S. Cl.
USPC ..... Plt./188

(58) Field of Classification Search
USPC ..... Plt./188

CPC ..... A01H 6/7454; A01H 5/08
See application file for complete search history.

(56) References Cited

U.S. PATENT DOCUMENTS

| | | | |
|---|---|---|---|
| PP14,627 | P3 | 3/2004 | Byrne et al. |
| PP14,629 | P3 | 3/2004 | Byrne et al. |
| PP28,077 | P3 | 6/2017 | Byrne et al. |

OTHER PUBLICATIONS

U.S. Appl. No. 19/336,355 filed Sep. 22, 2025, Byrne et al.
Ramming, 2005. Galaxy Peento Peach. HortScience 40(6):1921-1922.

*Primary Examiner* — Keith O. Robinson
(74) *Attorney, Agent, or Firm* — Dentons US LLP

(57) ABSTRACT

Disclosed is a new variety of *Prunus persica* named 'TRH4D144WN', which requires approximately 500 chilling units of dormancy, produces an acid-sweet, white-fleshed firm clingstone nectarine with a 70-90% medium to dark pink blush that matures in the early mid-season.

5 Drawing Sheets

Latin name of the genus and species of the plant claimed: *Prunus persica.*

Variety denomination: 'TRH4D144WN'.

BACKGROUND OF THE INVENTION

This invention relates to a nectarine tree and, more specifically, to a nectarine tree referred to as a variety of *Prunus persica* named 'TRH4D144WN', which requires approximately 500 chilling units of dormancy, produces acid-sweet, white-fleshed firm clingstone nectarine with a medium to dark pink blush over a white ground color that matures in the early mid-season. The present nectarine tree was the result of an ongoing Stone Fruit Breeding in College Station, Brazos County, Texas. To this end, controlled crosses were made each year to produce seedling populations from which improved progenies are evaluated and selected. 'TRH4D144WN' originated from a cross between 'Smooth Delight One' (patented) and 'Galaxy' (not patented). The seed from this cross was planted in 2013 at the experimental breeding plot in Floresville, TX. 'TRH4D144WN' was marked for subsequent observation in 2015 and noted as having exceptional characteristics. Two-year and older trees of the variety were subsequently evaluated during the 2017 through 2023 fruit growing seasons in Texas.

'TRH4D144WN' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach rootstock at the nursery site in Oakdale, CA. The variety was subsequently planted and evaluated at the experimental orchards in Texas (Somerville, 2018-2023; Pleasanton, 2018-2021). This evaluation clearly demonstrated that the re-propagated trees were true to the characteristics of the original seedling in all observable aspects.

SUMMARY OF THE INVENTION

The 'TRH4D144WN' nectarine produces acid-sweet, white-fleshed fruit that ripens in the early mid-season; produces a nectarine fruit that is firm and has a 70-90% medium to dark pink blush over a white ground color. The present variety of nectarine tree bears fruit that are ripe for commercial harvesting and shipment in early June when the fruit is grown in the medium chill zone of Texas. 'TRH4D144WN' ripens about 3 weeks later than its female parent, 'Smooth Delight One' (patented, U.S. Plant Pat. No. 28,077) and with its pollen parent, 'Galaxy' (Ramming, D.W. 2005. 'Galaxy' peento peach. HortScience 40 (6): 1921-1922, not patented). It differs from its female parent as it has acid-sweet flesh as compared to the subacid flesh of its female parent. It differs from its pollen parent 'Galaxy' as it is a round nectarine with acid-sweet flesh as compared to 'Galaxy' which is a peento peach with subacid flesh.

'TRH4D144WN' differs from 'Smooth Texan One' (patented, U.S. Plant Pat. No. 28,171) and 'Smooth Texan Two' (patented, U.S. Plant Pat. No. 28,360) acid-sweet nectarines as it has white rather than yellow flesh and ripens 3-4 weeks later. 'TRH4D144WN' also blooms ~3 days after 'Smooth Texan One' and ~9 days before 'Smooth Texan Two'.

'TRH4D144WN' differs from 'Smooth Delight One' and 'Smooth Delight Two' subacid nectarines as it has acid-sweet rather than subacid flavor, blooms about a week later and ripens about three weeks later than the commercial nectarines. 'TRH4D144WN' differs from 'Smooth Delight Two' as the new nectarine has white rather than yellow flesh color.

The new variety exhibits the potential to be commercialized in regions that have chilling requirements that are relatively low.

BRIEF DESCRIPTION OF THE DRAWINGS

This new variety of nectarine tree is illustrated by the accompanying photographs of 4 to 6-year old plants grown in Pleasanton and Somerville, Texas, as provided in FIGS. 1-5.

These photographs show the plant's typical fruit, foliage, and flowers, and the colors shown are as true as can be reasonably obtained by conventional photographic procedures.

DETAILED BOTANICAL DESCRIPTION

Figure 1:
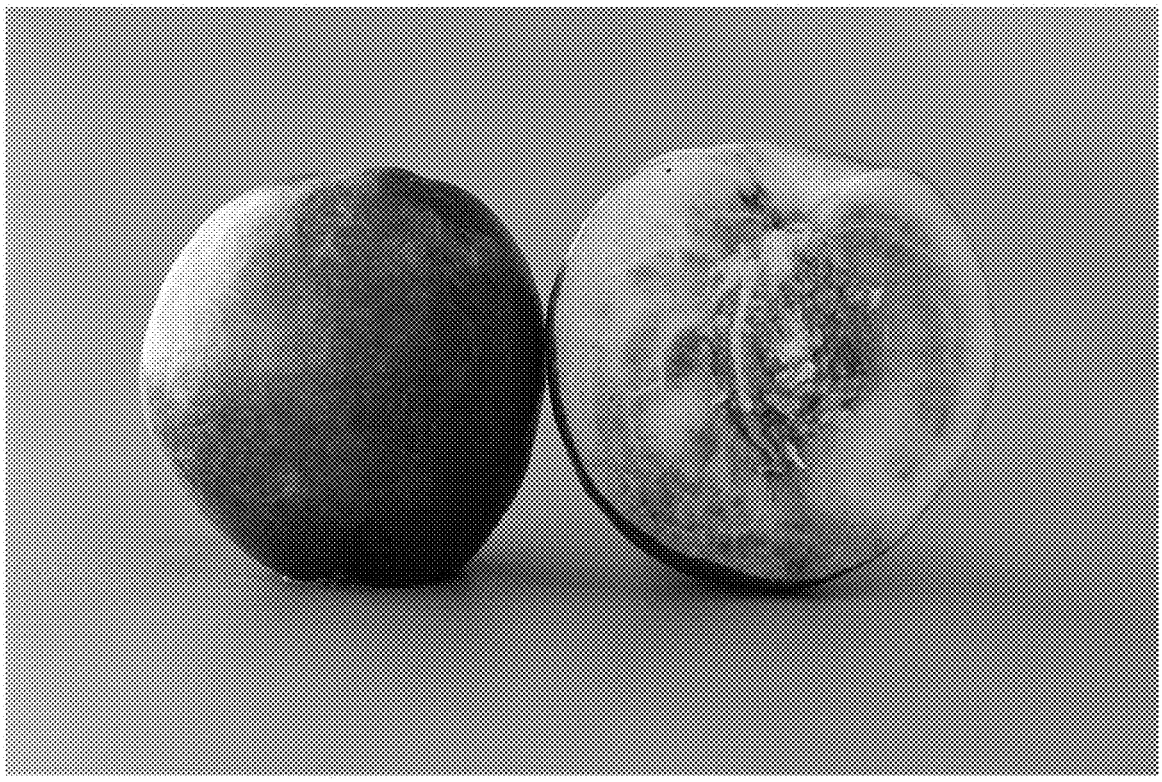
FIG. 1. Fruit of 'TRH4D144WN' harvested about 95 days after bloom in Pleasanton, Texas showing external and internal coloration.
Figure 2:
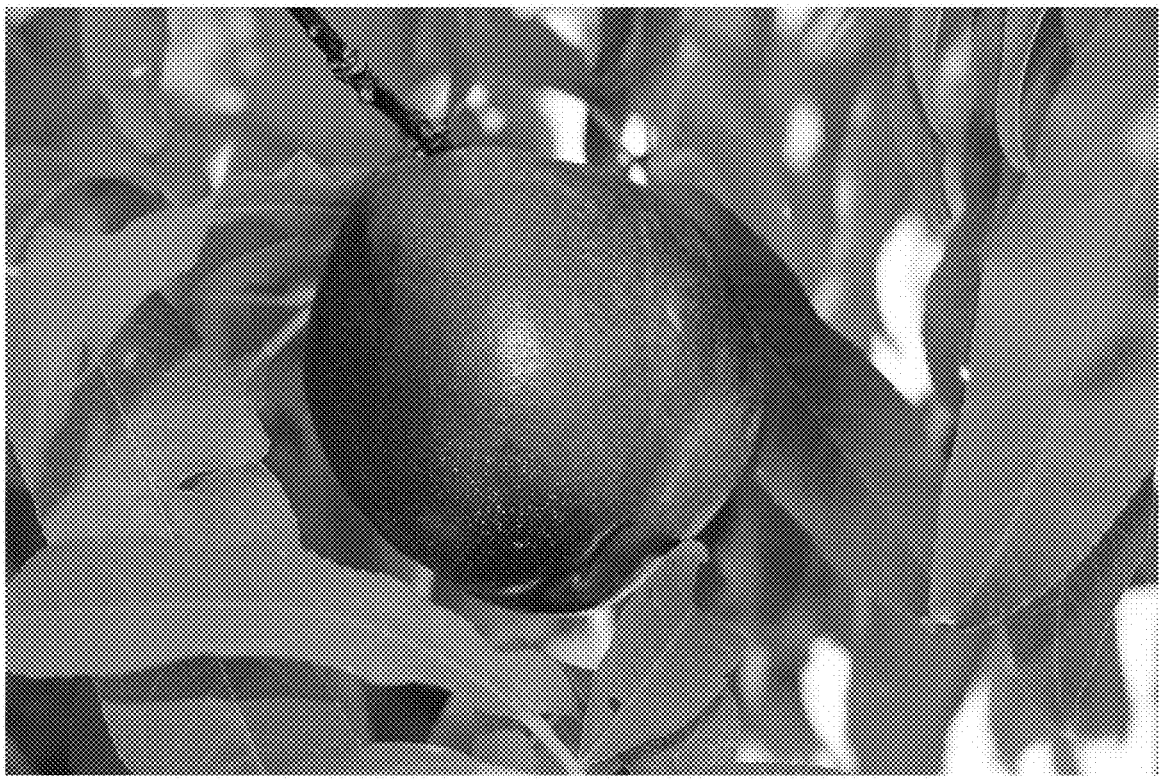
FIG. 2. 'TRH4D144WN' fruit harvested about 95 days after bloom in Somerville, Texas.
Figure 3:
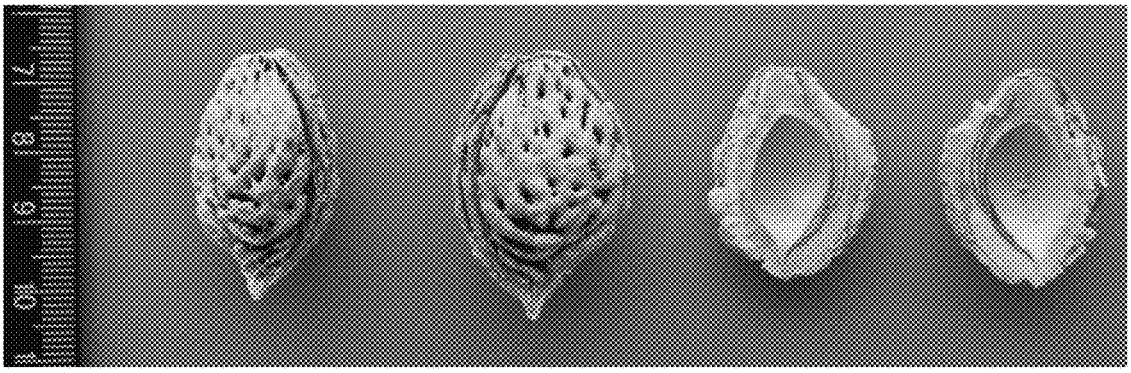
FIG. 3. Photograph of the endocarps of 'TRH4D144WN' nectarine. The ruler is in centimeters.
Figure 4:
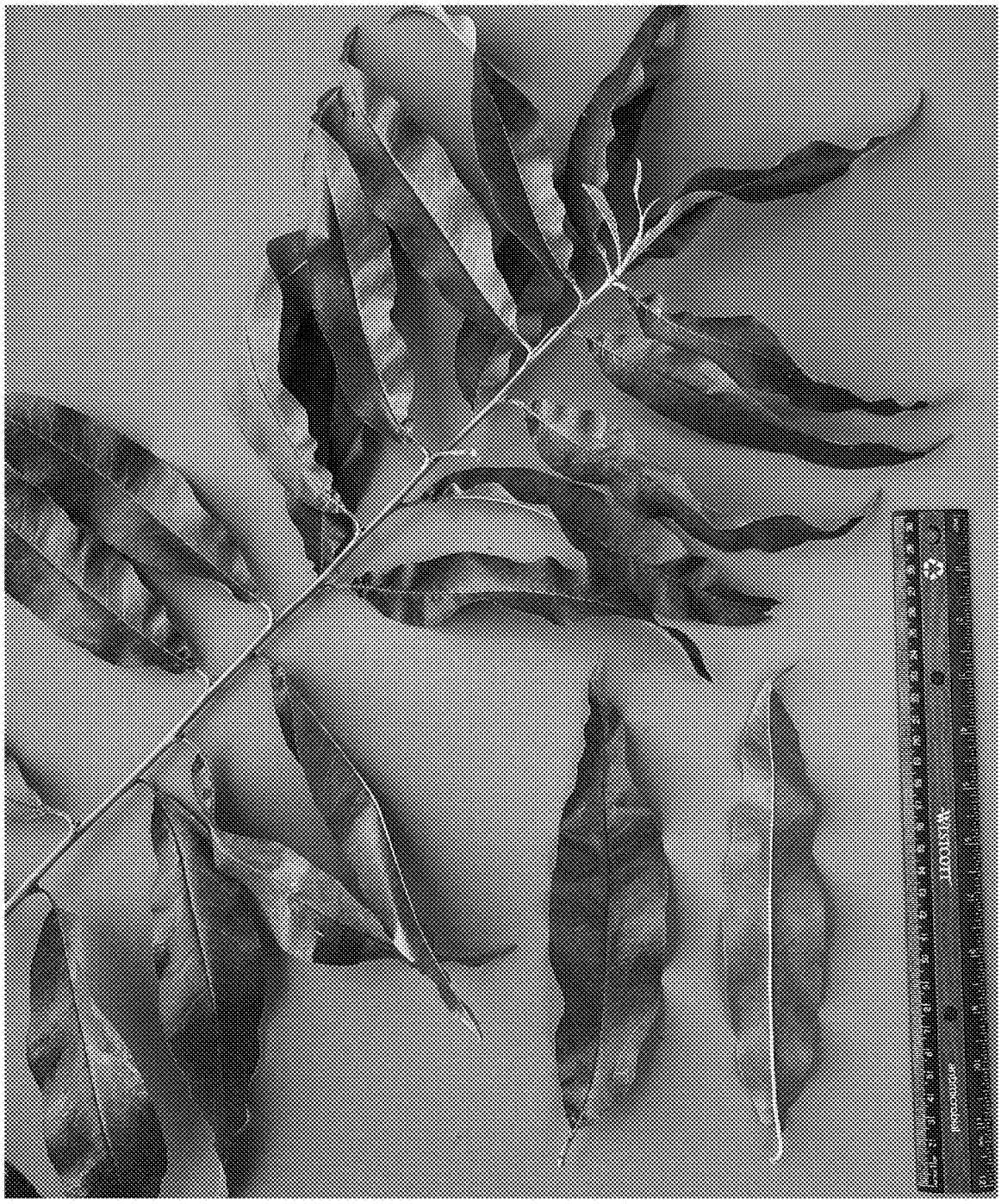
FIG. 4. A stem showing the leaves of 'TRH4D144WN' nectarine. The ruler is in centimeters.
Figure 5:
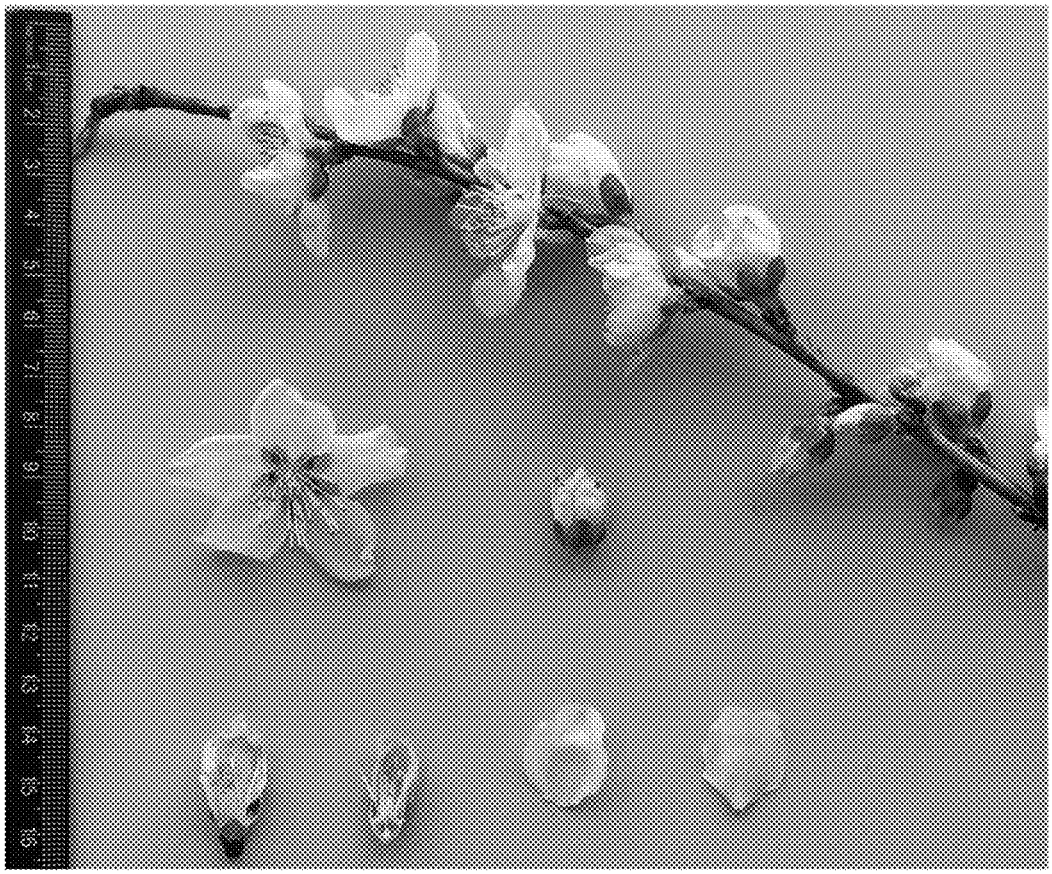
FIG. 5. A stem showing the flowers of 'TRH4D144WN' nectarine. The ruler is in centimeters.

Referring more specifically to the pomological details of this new and distinct variety of nectarine tree, the following has been observed under the ecological conditions prevailing at the experimental orchards in the medium chill zone of Texas (Pleasanton and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size.*—Generally average as compared to other common peach cultivars ripening in the early season of maturity.

*Height.*—6 feet (1.8 m) at the end of the 2024 growing season.

*Width.*—6 feet width (1.8 m) at the end of the 2024 growing season.

*Productivity.*—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. Trees often set more fruit than needed for a full crop. The recommended fruit spacing for early to mid-season ripening fresh market nectarine cultivars for a full crop is one fruit every 6-8" of one-year old fruiting wood.

*Shape.*—The 'TRH4D144WN' nectarine has been trained to an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth.*—The current season growth for the new variety was approximately 1 to 3 feet (0.3-0.9 m). Medium vigor as compared to other commercial cultivars in the medium chill zone of Texas. Regularity of Bearing — Regular in the absence of temperatures of 28° F. or below during bloom and considered hardy in the medium chill zone of Texas.

Trunk:

*Size.*—Approximately 2 inches (5 cm) in diameter and 6.5 inches (16.5 cm) in circumference when measured at a distance of approximately 12 inches (30.5 cm) above the soil level, at the end of the 2024 growing season on a three-year old tree.

*Bark texture.*—Considered moderately rough with numerous folds of papery scarf-like skin being present.

*Bark coloration.*—Variable, colors (RHS2001) present are 156D of the Greyed-White Group, 166A, 175A and 176A of the Greyed-Orange Group, 198D of the Greyed-Green Group and 201D of the Grey Group.

Branches:

*Thickness.*—Average (about 2.8 cm in diameter as measured 10 cm from the trunk on a three-year old tree) as compared to other varieties.

*Surface texture.*—Average and appearing furrowed on wood that is several years old.

*Lenticels.*—Numerous flat, oval lenticels present. The lenticels range in size from approximately 4 to 6 mm in width and were approximately 1 to 2 mm in height.

*Current season shoots.*—Surface texture-Substantially glabrous.

*Internode length.*—Approximately 2.5 to 4.0 cm as measured in the middle of a current season stem. Color of Mature Branches —The predominant colors (RHS2001) are 165A, 166B, 174A, 175A, 175B and 177A of the Greyed-Orange Group and N200D of the Brown Group.

Leaves:

*Size.*—Considered moderately short to medium for the species. Leaf measurements have been taken from vigorous upright current season growth approximately at mid- shoot.

*Leaf length.*—Approximately 127 to 146 mm.

*Leaf width.*—Approximately 30 to 37 mm.

*Leaf thickness.*—Less than 1 mm.

*Leaf form.*—Lanceolate.

*Leaf tip form.*—Acuminate.

*Leaf upper surface color* (*RHS*2001).—Green, approximately 146A and 146B of the Yellow-Green Group.

*Leaf lower surface color* (*RHS*2001).—Green, approximately 146B and 146C of the Yellow-Green Group.

*Leaf lower mid-vein color* (*RHS*2001).—Light yellow green 145C of the Yellow-Green Group.

*Leaf margins.*—Form — Considered crenate. Uniformity — Considered generally uniform.

*Leaf petioles.*—Length — Approximately 12 to 14 mm. Thickness — Approximately 1 mm. Color (RHS2001) — Pale green N144C, 145B and 145C of the Yellow-Green Group.

*Leaf glands.*—Size — Approximately 1 mm in height and less than 1 mm in width. Number — Generally 2 per leaf. Type — Reniform. Color (RHS2001) —

Brown, 166A of the Greyed-Orange Group, N199B of the Grey-Brown Group and 200A and 200B of the Brown Group.

*Leaf stipules.*—Length — Approximately 8 to 13 mm. Form — Lanceolate. Color (RHS2001) —Green, approximately 144A and 144B of the Yellow-Green Group. The stipules are early deciduous. Ratio of wood (leaf) buds to flowering buds —Generally 2 flower buds per vegetative bud.

Flowers:

*Floral buds.*—General — The floral buds are conic in form, and slightly appressed relative to the bearing shoot. Color (RHS2001) — The dormant buds are greyish brown (approximately 156A, 156B, 156C, and 156D of the Greyed-White Group, 165A, 166A, 174A, 175A, 176A, 176B and 177A of the Greyed-Orange Group, 178A of the Greyed-Red Group, 183A, 183B, 183C, 185A, N186C, 187A and 187B of the Greyed-Purple, 198A and 198B of the Greyed-Green Group, N199B of the Greyed-Brown Group, 200B, 200C and 200D of the Brown Group and 201B of the Grey Group). The buds are considered hardy in the medium chill zone of Texas. Mature Bud Length — Approximately 3 to 7 mm. Mature Bud Width — Less than 1 mm

*Blooming type.*—Mean date of full bloom in the medium chill zone of Texas was in late February (February 24$^{th}$ at Somerville), a few days after the commercial cultivar 'Texking'.

*Flower type.*—Showy.

*Flower size.*—Flower diameter at full bloom is approximately 36 to 48 mm.

*Bloom quantity.*—Considered abundant (approximately 0.5 to 1.0 flower per cm of one-year old fruiting wood).

*Flower bud frequency.*—Normally 2 per node.

*Petal size.*—Width — Approximately 16 to 17 mm Length — Approximately 21 to 22 mm

*Petal form.*—Broadly ovate.

*Petal Count.*—Generally 5 petals.

*Petal abaxial/adaxial color* (*RHS*2001).—Medium pink when young with the darker colors more prominent near the petal claw (62C, 62D, 65B, 65C, 65D, 69A and 69B of the Red-Purple Group).

*Petal claw.*—Form — The claw is considered truncate in shape. Length — Approximately 1 to 2 mm Width — Approximately 2 mm

*Petal margins.*—Generally considered variable, from nearly smooth to slightly undulate.

*Petal apex.*—Generally-The petal apices appear slightly rounded.

*Flower pedicel.*—Length — Average length of 2 mm. Thickness — Approximately 1 mm. Color (RHS2001) — A light green (144D, N144D, 145A and 145B of the Yellow-Green Group).

*Floral nectaries.*—Color (RHS2001) — Medium orange (17A, 17B, 21B, 21C, 22A and 23A of the Yellow-Orange Group).

*Sepals.*—Surface Texture — The surface has a short, fine, wooly texture. Size — Average Height 4.9 mm. Width 4.6 mm. Form — Ovate. Sepal Number — Five sepals per flower. Color (RHS2001) — Maroon with green and white. (59A, 59B, 59C, 60A and 60B of the Red-Purple Group, 144B, 144C, N144C, N144D and 145A of the Yellow-Green Group, 155A, 155B, 155C, 155D of the White Group, 178A of the Greyed-Red Group and 183A,183B, 183C, 185A, 185B and 187C of the Greyed-Purple Group).

*Floral cup* (*hypanthium*).—Surface Texture — Generally glabrous. Color (RHS2001) — Maroon with light green (approximately 59A, 59B, 59C, 60A and 60B of the Red-Purple Group, 144B, 144C, N144C, N144D and 145A of the Yellow-Green Group, 178A of the Greyed-Red Group and 183A,183B, 183C, 185A, 185B and 187C of the Greyed-Purple Group).

*Anthers.*—Color (RHS2001) — Medium orange (approximately N25A and 28A of the Orange Group and 31A of the Orange-Red Group).

*Pollen Production.*—Pollen is abundant and is a dark yellow color (RHS2001) (approximately 13A and 13B of the Yellow Group and 14A, 14B, 15A, 15B, 15C and 16A of the Yellow-Orange Group).

*Filaments.*—Size — Variable in length, approximately 11 to 14 mm, with the filaments slightly shorter than the pistil and below the height of the petals at the pink bud stage. Color (RHS2001) — White (approximately 155A, 155B, 155C, 155D of the White Group) with the darker colors more prominent with advanced maturity.

*Pistil.*—General — Slightly longer relative to the general anther height and below the height of the petals in the pink bud stage. Length — Approximately 16 to 19 mm, including the ovary. Color (RHS2001) — Considered a light yellow-green when young (approximately 1A, 1B, 1C, and 1D of the Green-Yellow Group) with the darker colors more prominent with advancing senescence.

*Surface texture.*—Is generally glabrous.

Fruit:

*Maturity when described.*—The present variety of fruit is described, as it would be found in its firm ripe condition at full commercial maturity. Under the ecological conditions prevailing in the medium chill zone of Texas it would be ripe in late May to Early June. The average ripe date at Pleasanton and Somerville experimental plots were May 26$^{th}$ and June 2$^{nd}$ respectively.

*Size.*—General-Medium to medium large for the season and considered uniform. Average Cheek Diameter — Approximately 63 to 64 mm Average Suture Diameter — Approximately 63 to 64 mm Average Axial Diameter — Approximately 52 to 60 mm

*Fruit form.*—Generally considered truncate with unequal halves. The fruit exhibits less symmetry when comparing the suture height with the line opposite the suture and generally asymmetrical when viewed from the apical aspect.

*Fruit suture.*—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Medium to dark pink, 46A and 53A of the Red Group, 59A, 59B and 60A of the Red-Purple Group and 187B and 187C of the Greyed-Purple Group.

*Ventral surface.*—Form — Considered uniform.

*Stem cavity.*—Width — Approximately 19 to 21 mm. Length — Approximately 24 to 26 mm. Depth — Approximately 9 to 12 mm.

*Fruit base.*—Flat.

*Fruit apex.*—Flat.

*Fruit stem.*—Length — 9 to 10 mm. Thickness — 2 to 4 mm. Color (RHS2001) — Light to medium green, 144D, N144D, 145A, 145B and 146D of the Yellow-Green Group.

*Fruit skin.*—Generally considered medium or average in thickness. Surface Pubescence — Absent. Skin Acidity — Considered neutral. Tenacious to Flesh — Yes at commercial maturity. Tendency to Crack — Not observed. Skin Color (RHS2001) — Generally-Variable, with approximately 70-90% of the fruit surface covered with a medium to dark pink blush. Blush Color (RHS2001) — Medium to dark pink, 46A and 53A of the Red Group, 59A, 59B and 60A of the Red-Purple Group and 187B and 187C of the Greyed-Purple Group. Skin Ground Color (RHS2001) — White to very light green, 1C, and 1D of the Green-Yellow Group and 155A, 155B, 155C and 155D of the White Group.

*Flesh color* (*RHS*2001).—White with dark pink, 58A, 59C, 60D, 61B and 63A of the Red- Purple Group, 155A, 155B, 155C and 155D of the White Group and 187D of the Greyed-Purple Group.

*Flesh fibers.*—Present throughout the flesh.

*Stone cavity color* (*RHS*2001).—White with dark pink, 58A, 59C, 60D, 61B and 63A of the Red-Purple Group, 155A, 155B, 155C and 155D of the White Group and 187D of the Greyed-Purple Group.

*Flesh texture.*—Considered firm at commercial maturity.

*Ripening.*—Generally the fruit of the present variety ripens evenly.

*Flavor.*—Considered sweet (average Brix 12.6) and rich, with slightly acidic flavor.

Stone:

*Attachment.*—Clingstone at commercial maturity.

*Stone size.*—Generally considered moderately large relative to the ratio of stone to fruit size. Length — Approximately 35 to 37 mm. Width — Approximately 23 to 24 mm. Thickness — Approximately 17 to 18 mm.

*Fibers.*—Generally a few fibers are sporadically attached along the surface of the stone.

*Stone form.*—Elliptical to ovate.

*Stone base angle.*—Medium.

*Apex shape.*—Wide.

*Stone shape.*—Elongated.

*Stone surface.*—Surface Texture — Single and chains of pits. Ridges — Numerous fine ridges are present basally and converge towards the base of the stone.

*Ventral edge.*—Truncated.

*Dorsal edge.*—Shape — Grooved and having moderately rough edges.

*Stone color* (*RHS*2001).—The color of the dry stone is medium brown, 165B and 165C of the Greyed-Orange Group. The color of the inside surface of the endocarp is primarily tan to medium brown, 164B, 164C, 165C and 165D of the Greyed-Orange and N199C of the Grey-Brown Group.

*Tendency to split.*—Splitting is relatively uncommon.

*Kernel.*—The kernel fills the endocarp at harvest and measures approximately 5-6 mm in thickness, 10-11 mm in width, and 19 mm in length. The color (RHS2001) of the fresh kernel are light to medium brown, 163A, 164A, 164B, 164C, 165B and 165C of the Greyed-Orange Group. When dried the shriveled kernels measure approximately 2-3 mm in thickness, 9- 10 mm in width and 16-18 mm in length. The colors of the shriveled kernels are primarily medium brown, 164A, 165B, 165C and N167A of the Greyed-Orange Group and N199D of the Grey-Brown Group.

*Use.*—The subject variety, 'TRH4D144WN', is a medium chill nectarine tree of early mid-season maturity, which produces acid-sweet, white-fleshed nectarine fruit which are firm with a 70-90% maroon blush over a white ground color, and which are useful for the fresh fruit market.

*Keeping quality.*—Average. Retains firmness and flavor after 14 days of refrigeration at 3-5° C.

*Resistance to insects and disease.*—No atypical resistances/susceptibilities were noted under normal cultural practices to date.

*Shipping quality.*—Average. Fruit does not develop internal breakdown and retains good firmness and eating quality after 14 days of refrigeration at 3-5° C.

Although the new variety of nectarine tree possesses the described characteristics when grown under the ecological conditions prevailing in the medium chill zone of Texas, it will be understood that variations of the usual magnitude and characteristics incident to the changes in growing conditions, fertilization, pruning, and pest control are to be expected.

What is claimed is:

1. A new and distinct variety of nectarine tree named 'TRH4D144WN', as illustrated and described herein.

* * * * *